(12) United States Patent
Li et al.

(10) Patent No.: US 12,005,273 B2
(45) Date of Patent: Jun. 11, 2024

(54) CALIBRATION METHOD, DEVICE AND STORAGE MEDIUM OF RADIOTHERAPY EQUIPMENT

(71) Applicant: OUR UNITED CORPORATION, Xi'an (CN)

(72) Inventors: Jinsheng Li, Xi'an (CN); Hao Yan, Xi'an (CN)

(73) Assignee: Our United Corporation, Shaanxi (CN)

( * ) Notice: Subject to any disclaimer, the term of this patent is extended or adjusted under 35 U.S.C. 154(b) by 1226 days.

(21) Appl. No.: 16/618,766

(22) PCT Filed: Jun. 2, 2017

(86) PCT No.: PCT/CN2017/087078
§ 371 (c)(1),
(2) Date: Dec. 2, 2019

(87) PCT Pub. No.: WO2018/218684
PCT Pub. Date: Dec. 6, 2018

(65) Prior Publication Data
US 2020/0129785 A1    Apr. 30, 2020

(51) Int. Cl.
*A61N 5/10* (2006.01)
(52) U.S. Cl.
CPC .... *A61N 5/1075* (2013.01); *A61N 2005/1076* (2013.01)
(58) Field of Classification Search
CPC .............. A61N 5/1075; A61N 2005/1076
See application file for complete search history.

(56) References Cited

U.S. PATENT DOCUMENTS

| | | | |
|---|---|---|---|
| 2010/0303210 A1 | 12/2010 | Beaumont et al. | |
| 2014/0270077 A1 | 9/2014 | Etmektzoglou | |
| 2015/0224342 A1* | 8/2015 | Baltes | A61B 6/486 378/62 |

FOREIGN PATENT DOCUMENTS

| | | |
|---|---|---|
| CN | 103517736 A | 1/2014 |
| CN | 103768724 A | 5/2014 |

(Continued)

OTHER PUBLICATIONS

First Office Action in Chinese application No. 201780011883.8 dated Feb. 3, 2020.

(Continued)

*Primary Examiner* — Carrie R Dorna
(74) *Attorney, Agent, or Firm* — Knobbe, Martens, Olson & Bear, LLP

(57) ABSTRACT

Provided are a calibration method, device and storage medium of radiotherapy equipment. The calibration method of the radiotherapy equipment adopts an imaging body disposed within a preset distance range of an isocenter of radiotherapy equipment to perform error calibration on the radiotherapy equipment, and includes: imaging the imaging body through an imaging system to obtain an actual image of the imaging body; determining an image deviation between the actual image and a theoretical image of the imaging body, wherein the theoretical image is determined in advance based on a theoretical position of the imaging system and a spatial position of the imaging body in a rack; and determining a system error of imaging system based on the image deviation. Thus, the imaging system is calibrated without moving a treatment couch. The calibration accuracy of imaging system is not influenced by movement precision of treatment couch. The calibration accuracy is improved.

11 Claims, 5 Drawing Sheets

(a)

(b)

(56) References Cited

FOREIGN PATENT DOCUMENTS

| CN | 104043195 A | 9/2014 |
|----|-------------|--------|
| CN | 104414662 A | 3/2015 |
| CN | 104587609 A | 5/2015 |
| CN | 105833431 A | 8/2016 |
| GB | 2530790 A | 4/2016 |

OTHER PUBLICATIONS

International Search Report in PCT application No. PCT/CN2017/087078 dated Mar. 6, 2018.
Third Office Action of Chinese Patent Application No. 201780011883.8—15 pages (dated Dec. 18, 2020).

* cited by examiner

| 101 | Imaging an imaging body in an image calibration tooling through an imaging system to obtain an actual image of the imaging body |

| 102 | Determining an image deviation between the actual image and a theoretical image of the imaging body, wherein the theoretical image is determined in advance based on a theoretical position of the imaging system and a spatial position of the imaging body in radiotherapy equipment |

| 103 | Determining a system error of the imaging system based on the image deviation |

CALIBRATION METHOD, DEVICE AND STORAGE MEDIUM OF RADIOTHERAPY EQUIPMENT

TECHNICAL FIELD

The present disclosure relates to the field of medical equipment, and more particularly to a calibration method, device and storage medium of radiotherapy equipment.

BACKGROUND

Radiotherapy equipment is equipment that can perform noninvasive or minimally invasive treatment by using artificial or natural rays on patients suffering from tumors or other functional diseases. In practice, it is usually necessary to determine an accurate location of a radiotherapy target before the radiotherapy treatment to ensure the accuracy and effectiveness of the radiotherapy. However, a system error of the radiotherapy equipment itself may affect the location accuracy and treatment accuracy of the radiotherapy equipment. Hence, the radiotherapy equipment is often required to be calibrated before being located to obtain a system error of the radiotherapy equipment, so as to perform the error correction on the radiotherapy equipment or perform the error compensation on the locating process of the radiotherapy equipment based on the system error.

Figure 1A:
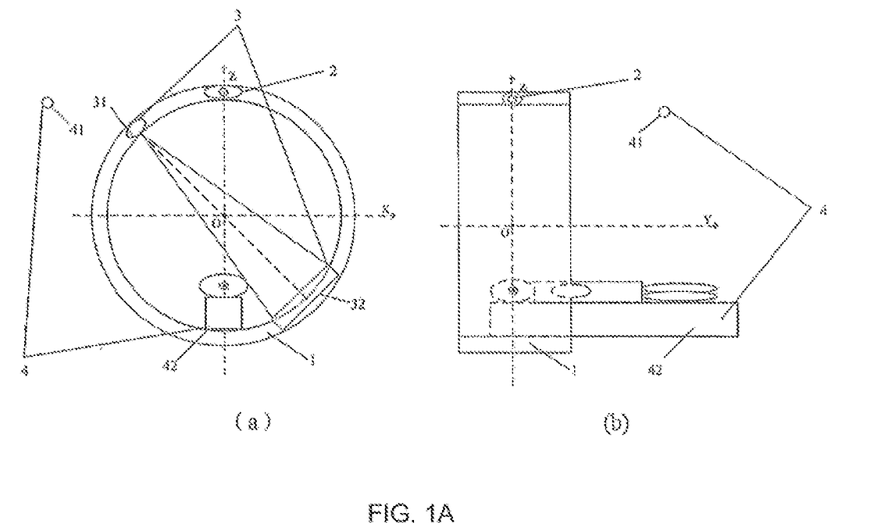
Figure 1B:
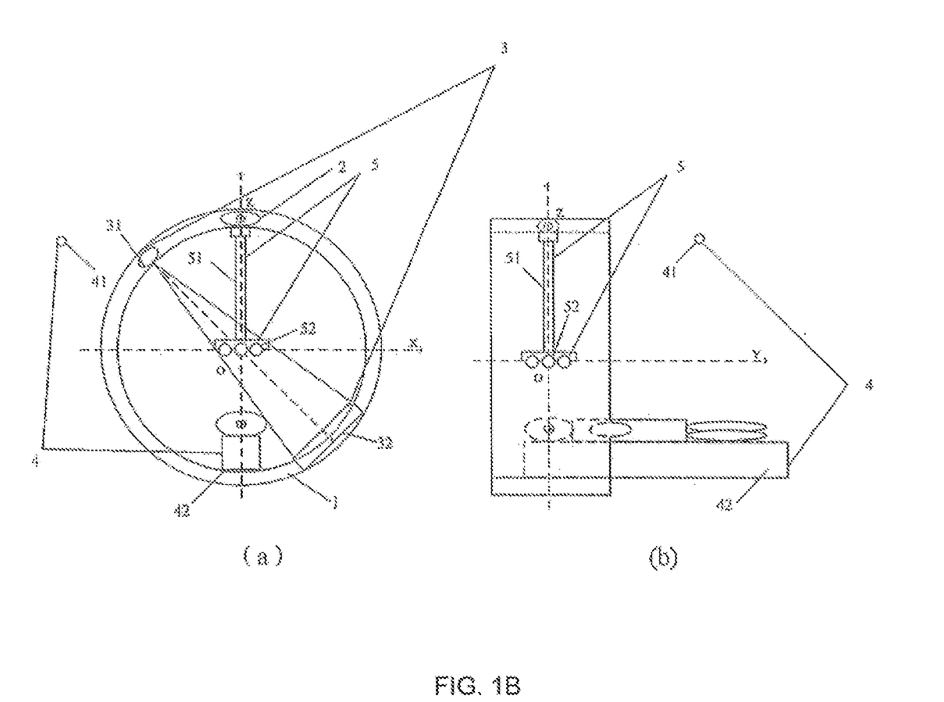

As shown in FIG. 1A(a) and FIG. 1A(b), the radiotherapy equipment generally includes a rack 1, a treatment head 2, an imaging system 3 and a positioning system 4 disposed outside the rack. Here, the rack 1 may be a roller, a C-shaped arm or other structures. In FIG. 1A(a) and FIG. 1A(b), only the rack being a roller structure is taken as an example. The treatment head 2 is mounted on the rack 1 and may be driven to rotate around a Y-axis under the rotation of the rack, such that a radiotherapy treatment may be performed on the radiotherapy target by means of rays emitted by the treatment head 2. The Y-axis is a coordinate axis perpendicular to a plane where an X-axis and a Z-axis are located. The imaging system 3 includes an imaging source 31 located on the rack 1 and a flat panel detector 32 disposed in a position, opposite to the imaging source 31, on the rack 1, and is used to image the radiotherapy target through the imaging source 31 and the flat panel detector 32 to guide the radiotherapy. The positioning system 4 includes a locating reference device 41 and a treatment couch 42. Taking the locating reference device 41 as a benchmark, the treatment couch 42 is moved, so as to locate the radiotherapy target on the treatment couch 42. That is, the radiotherapy target on the treatment couch can be moved to a preset position.

Since the imaging system is a core component of an image-guided radiotherapy system, it is a key system for determining the locating accuracy of the treatment, and the system error thereof determines an error in the radiotherapy treatment of the radiotherapy equipment. Thus, calibration of the imaging system is a basis for calibration of the radiotherapy equipment. In order to realize calibration of the imaging system, a model body that can replace the radiotherapy target may be placed on the treatment couch, and reference points can be disposed on the model body. The reference points may be determined according to a plurality of gauge points on the surface of the model body. Herein, a calibration method of the imaging system may be specifically described as follows. In accordance with location of the locating reference device, the treatment couch on which the model body is placed is moved to make the reference point on the model body spatially overlap a central point of the positioning system. Based on a known position relationship between the central point of the positioning system and an isocenter of the radiotherapy equipment, the treatment couch is moved along the Y axis to put the model body into the rack. The isocenter of the radiotherapy equipment refers to an intersection point of rays emitted by the treatment head in different directions along with rotation of the rack, for example, a coordinate origin O of a three-dimensional coordinate system where the X axis, the Y axis and the Z axis are located. After that, the model body is imaged by means of the imaging source and the flat panel detector so as to obtain an actual image of the model body. The actual image of the model body is compared with its theoretical image to obtain an image deviation. The theoretical image of the model body is obtained through beforehand image scanning (for example, CT) of the model body. The system error of the imaging system is determined based on the image deviation.

Since the above-mentioned calibration method needs to be implemented through positioning of the model body and movement of the treatment couch, the calibration accuracy of the imaging system may be influenced by the positioning accuracy of the model body and the accuracy of the treatment couch's position. However, as the treatment couch and the rack are separated systems, whether the radiotherapy target on the treatment couch can be moved to the preset position or not depends on the accuracy of a driving system of the treatment couch. In case of abnormity or accuracy reduction of the drying system, there will be a deviation between the position to which the radiotherapy target on the treatment couch is actually moved and the preset position. This further leads to inaccurate calibration of the imaging system. When positioning the model body by means of the positioning system, there may exist a human error or a positioning system error, which may further result in inaccurate calibration of the imaging system.

SUMMARY

There are provided a calibration method of radiotherapy equipment, an image calibration tooling, a storage medium and a program product in embodiments of the present disclosure. The technical solutions are as below.

In a first aspect, there is provided an error calibration method of radiotherapy equipment. The radiotherapy equipment includes an imaging system. An imaging body disposed within a preset distance range of an isocenter of the radiotherapy equipment is adopted for error calibration of the radiotherapy equipment. The error calibration method includes: imaging the imaging body through the imaging system to obtain an actual image of the imaging body; determining an image deviation between the actual image and a theoretical image of the imaging body, the theoretical image being obtained in advance based on a theoretical position of the imaging system and a spatial position of the imaging body in the radiotherapy equipment; and determining a system error of the imaging system based on the image deviation.

In a second aspect, based on the calibration method according to the first aspect, there is provided a calibration method of a positioning system.

In a third aspect, there is provided a location method of a radiotherapy target. Radiotherapy equipment of which calibration is accomplished by using the error calibration method in the first aspect may be adopted to locate the radiotherapy target. The location method includes: acquiring a scanned image of the radiotherapy target placed on a treatment couch, the radiotherapy target being provided with a reference point thereon; positioning the radiotherapy target on the treatment couch through a positioning system to enable that the reference point on the radiotherapy target overlaps a central point of the positioning system; moving the treatment couch based on a position relationship between the central point of the positioning system and an isocenter of the radiotherapy equipment, to put the radiotherapy target into the radiotherapy equipment; imaging the radiotherapy target through an imaging system to obtain an actual image of the radiotherapy target; and moving the radiotherapy target to a preset position based on the actual image and the scanned image of the radiotherapy target.

In a fourth aspect, there is provided an image calibration tooling, which comprises a support and at least one imaging body connected to an end of the support. By connecting the image calibration tooling to radiotherapy equipment of which calibration is accomplished by the error calibration method according the first aspect, the at least one imaging body may be located within a preset distance range of an isocenter of the radiotherapy equipment. Error calibration may be performed on the radiotherapy equipment.

In a fifth aspect, there is provided an error calibration device of radiotherapy equipment. The radiotherapy equipment includes an imaging system. An imaging body disposed within a preset distance range of an isocenter of the radiotherapy equipment is adopted to calibrate the radiotherapy equipment. The error calibration device includes: a first imaging module configured to image the imaging body through the imaging system to obtain an actual image of the imaging body; a first determination module configured to determine an image deviation between the actual image and a theoretical image of the imaging body, the theoretical image being obtained in advance based on a theoretical position of the imaging system and a spatial position of the imaging body in the radiotherapy equipment; and a second determination module configured to determine a system error of the imaging system based on the image deviation.

In a sixth aspect, there is provided a locating device of a radiotherapy target. Radiotherapy equipment of which calibration is accomplished by the error calibration device in the fourth aspect is adopted to locate the radiotherapy target. The locating device includes: a third acquisition module configured to acquire a scanned image of the radiotherapy target placed on a treatment couch, the radiotherapy target being provided with a reference point thereon; a third positioning module configured to position the radiotherapy target on the treatment couch through a positioning system to enable that the reference point on the radiotherapy target overlaps a central point of the positioning system; a third movement module configured to move the treatment couch based on a position relationship between the central point of the positioning system and an isocenter of the radiotherapy equipment, to put the radiotherapy target into the radiotherapy equipment; a fifth imaging module configured to image the radiotherapy target through an imaging system to obtain an actual image of the radiotherapy target; and a fourth movement module configured to move the radiotherapy target to a preset position based on the actual image and the scanned image of the radiotherapy target.

In a seventh aspect, there is provided a computer readable storage medium in which an instruction is stored. When the computer readable storage medium runs on a computer, the computer executes any error calibration method of the radiotherapy equipment in the first aspect or any location method of the radiotherapy target in the third aspect.

In an eighth aspect, there is provided a computer program product including an instruction. When the computer program product runs on a computer, the computer executes any error calibration method of the radiotherapy equipment in the first aspect or any location method of the radiotherapy target in the third aspect.

In a ninth aspect, there is provided an error calibration device of radiotherapy equipment comprising an imaging system, wherein an imaging body disposed within a preset distance range of an isocenter of the radiotherapy equipment is adopted to calibrate the radiotherapy equipment, and the error calibration device comprises a first processor; and a first memory arranged to store an instruction executable by the first processor, wherein the first processor is configured to: image the imaging body through the imaging system to obtain an actual image of the imaging body; determine an image deviation between the actual image and a theoretical image of the imaging body, the theoretical image being obtained in advance based on a theoretical position of the imaging system and a spatial position of the imaging body in the radiotherapy equipment; and determine a system error of the imaging system based on the image deviation.

In a tenth aspect, there is provided a locating device of a radiotherapy target, wherein radiotherapy equipment of which calibration is accomplished by the calibration method according to the ninth aspect is adopted to locate the radiotherapy target; and the locating device comprises a second processor; and a second memory arranged to store an instruction executable by the second processor, wherein the second processor is configured to: acquire a scanned image of the radiotherapy target placed on a treatment couch, the radiotherapy target being provided with a reference point thereon; position the radiotherapy target on the treatment couch through a positioning system to enable that the reference point on the radiotherapy target overlaps a central point of the positioning system; move the treatment couch based on a position relationship between the central point of the positioning system and an isocenter of the radiotherapy equipment, to put the radiotherapy target into the radiotherapy equipment; image the radiotherapy target through an imaging system to obtain an actual image of the radiotherapy target; and move the radiotherapy target to a preset position based on the actual image and the scanned image of the radiotherapy target.

BRIEF DESCRIPTION OF THE DRAWINGS

In order to illustrate the technical solutions of the embodiments provided by the present disclosure more clearly, a brief introduction may be given hereinafter to the drawings that may be used in the description of the embodiments. Apparently, the drawings in the description below are merely for illustrating some embodiments of the present disclosure, and other drawings may be obtained by those skilled in the art according to these drawings without delivering any creative labor.

FIG. 1A(a) is a front view of a radiotherapy equipment in the related art;

FIG. 1A(b) is a side view of a radiotherapy equipment in the related art;

FIG. 1B(a) is a front view of a radiotherapy equipment provided in an embodiment of the present disclosure;

FIG. 1B(b) is a side view of radiotherapy equipment provided in an embodiment of the present disclosure;

DETAILED DESCRIPTION

To make the objectives, technical solutions and advantages of the present disclosure clearer, the followings will describe the embodiments of the present disclosure in detail with reference to the drawings.

For the sake of understanding, the terms, application scenarios and implementation environments involved in the embodiments of the present disclosure are introduced prior to the detailed explanation of the embodiments of the present disclosure.

Firstly, the terms in the embodiments of the present disclosure are explained.

Isocenter of Radiotherapy Equipment

An isocenter of the radiotherapy equipment refers to an intersection point of multiple radioactive rays emitted by a treatment head in different directions along with rotation of a rack. In practice, the isocenter of the radiation equipment is usually located at a central point of a rack.

Imaging Central Point of Imaging System

An imaging central point of an imaging system refers to an intersection point of multiple radioactive rays emitted by an imaging source in different directions along with rotation of the rack. In practice, the imaging central point of an imaging system is also usually located at the central point of the rack. That is, the imaging central point of the imaging system usually coincides with the isocenter of the radiotherapy equipment.

Therapeutic Target

A therapeutic target refers to a diseased region where a radiotherapy treatment is required. During the radiotherapy treatment, radioactive rays may irradiate in different directions and converge at the therapeutic target.

Secondly, the application scenarios of the embodiments of the present disclosure are introduced.

The embodiments of the present disclosure are applied to such scenarios as the radiotherapy treatment on a radiotherapy target by means of radiotherapy equipment, measurement of radiation dose and verification of QA (Quality Assurance) measurement calibration. QA measurement calibration refers to that a certain quality parameter of the radiotherapy equipment is measured to obtain an actual measured value, then a difference between the actual measured value and a theoretical measured value or a historical measured value is determined, and an accuracy range of the radiotherapy equipment is determined according to the difference. Before the treatment and measurement, in order to guarantee an accuracy of the treatment and measurement, it is usually required to calibrate the radiotherapy equipment first. That is, a system error of the radiotherapy equipment is determined, and error compensation is performed on the radiotherapy equipment based on the system error.

At last, an introduction is given to the environments in which the embodiments of the present disclosure are implemented.

The embodiments of the present disclosure are applied to radiotherapy equipment having an imaging system. To make it easier to understand, the followings will describe the radiotherapy equipment in detail with reference to the drawings.

As shown in FIG. 1B(a) and FIG. 1B(b), the radiotherapy equipment comprises a treatment head 2 and an imaging system 3. For accurate calibration in the imaging system 3, an image calibration tooling 5 is utilized to calibrate the imaging system 3.

Herein, the image calibration tooling 5 comprises an imaging body 52 disposed within a preset distance range of an isocenter of the radiotherapy equipment. Specifically, the image calibration tooling 5 comprises a support 51 and at least one imaging body 52 connected to an end of the support 51. The image calibration tooling 5 may be mounted on the treatment head 2 or other positions of a rack, as long as the at least one imaging body 52 is located within the preset distance range of the isocenter of the radiotherapy equipment. The preset distance range of the isocenter of the radiotherapy equipment refers to a location at or nearby the isocenter of the radiotherapy equipment.

Herein, the imaging body 52 may be in a shape of sphere, cube or others. Taking the shape of sphere as an example, the sphere may be made of metal or other materials, and may be a solid sphere or a hollow sphere, which are not limited in the embodiments of the present disclosure.

Herein, the support 51 may be of a cylinder or other connecting structures. The support 51 has one end connected to the treatment head 2 and the other end connected to at least one imaging body 52. In an implementation, the end, connected to the imaging body 52, of the support 51 may comprise a non-metallic connecting piece to which the at least one imaging body 52 is connected.

Figure 1C:
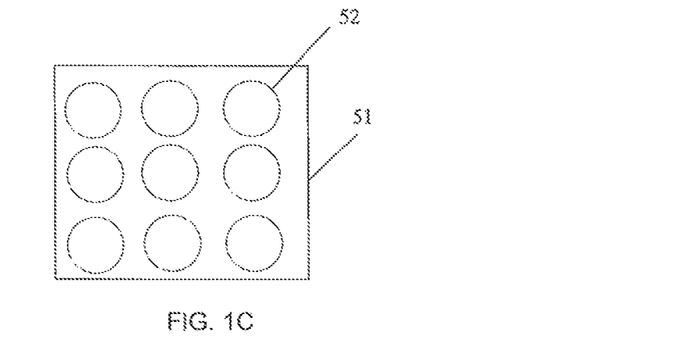
FIG. 1C is an enlarged view of an end of a support 51 provided in an embodiment of the present disclosure.

Herein, the at least one imaging body 52 may be arranged in random or in a specific order. Exemplarily, the at least one imaging body 52 may be arranged as an imaging body matrix. As shown in FIG. 1C, when the number of the at least one imaging body 52 is nine, the nine imaging bodies 52 may be arranged into a three-row three-line matrix. That is, there are three imaging bodies 52 in each row and as each line.

Furthermore, in order to facilitate calibration of the imaging system, one of the at least one imaging bodies 52 may be located at the isocenter of the radiotherapy equipment. In the embodiments, for example, the isocenter of the radiotherapy equipment serves as an origin O of coordinates.

In addition, the radiotherapy equipment further comprises a rack 1 (for example, the rack 1 is a roller in FIG. 1B(a) and FIG. 1B(b)). The treatment head 2 and the imaging system 3 are mounted on the rack 1 and may be driven to rotate around a Y axis by rotation of the rack 1. As the frame 1 rotates, the image system 3 should theoretically have the same imaging of the imaging body 52 at various angles of rotation. If they are not the same, it means that the imaging system has a system error. Thus, the system error of the imaging system may be determined subsequently according to whether the imaging of the imaging body 52 at the respective rotation angle is the same or not.

Herein, the image calibration tooling 5 and the treatment head 2 may be fixedly or movably connected. In practice, the image calibration tooling 5 and the treatment head 2 may be in movable connection for ease of installation. That is, when the imaging system needs to be calibrated, the image calibration tooling 5 may be mounted on the treatment head 2. After being utilized to complete calibration of the imaging system 3, the image calibration tooling 5 may also be taken down from the treatment head 2. Hence, a subsequent radiotherapy process of the treatment head 2 may not be influenced.

Specifically, the image calibration tooling 5 and the treatment head 2 may be connected by means of a movable connecting piece. The movable connecting piece may be an adsorption device through which the image calibration tooling 5 may be adsorbed onto the treatment head 2.

Alternatively, the movable connecting piece may be a screw nut through which the image calibration tooling 5 may be mounted on the treatment head 2. Certainly, the movable connecting piece may also be other types of movable connecting pieces, which is not limited in the embodiments of the present disclosure.

Furthermore, in order to improve the calibration accuracy, the image calibration tooling 5 is mounted on a reference plane of the treatment head 2. This reference plane refers to a lower surface that is parallel to a central horizontal plane of the rack 1.

Herein, the imaging system 3 comprises an imaging source 31 located on the rack 1 and a flat panel detector 32 disposed in a position, opposite to the imaging source 31, on the rack 1, and is configured to image a radiotherapy target by means of the imaging source 31 and the flat panel detector 32. When the radiotherapy target is imaged, the imaging source 31 may emit x rays to irradiate the radiotherapy target. The flat panel detector may detect the x rays that penetrate the radiotherapy target and send a detection signal to an image system of the radiotherapy equipment. The image system may generate an image of the radiotherapy target according to the received detection signal.

In addition, the radiotherapy equipment may further comprise a positioning system 4. The positioning system 4 comprises a locating reference device 41 and a treatment couch 42, and is configured to move the treatment couch 42 relative to the locating reference device 41 to position the radiotherapy target on the treatment couch 42.

Herein, the locating reference device 41 is configured to determine the position of a central point of the positioning system 4, such that the treatment couch can be moved according to the position of the central point of the positioning system 4. Thus, a reference point on a model body or the radiotherapy target that is placed on the treatment couch may overlap the central point of the positioning system 4. The treatment couch 42 is configured to place the model body or the radiotherapy target, and may be moved in a six dimensional space. That is, the treatment couch may be moved along and rotated around three coordinate axes including an X axis, a Y axis and a Z axis.

Figure 1D:
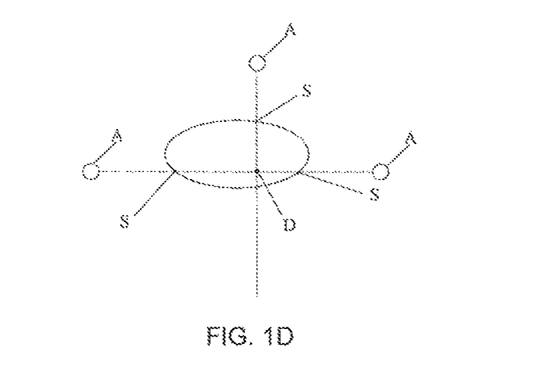
FIG. 1D is a schematic view of positioning of a positioning system provided in an embodiment of the present disclosure.

In practice, the locating reference device 41 may be a laser locating system, or a body surface imaging system or the like. The laser locating system is taken as an example. The laser locating system may comprise a plurality of laser sources. An intersection of light beams emitted by the plurality of laser sources is the central point of the positioning system. When the body position of the model body or the radiotherapy target is positioned, the light beams emitted by the plurality of laser sources may be utilized to locate the reference point of the model body or the radiotherapy target.

As shown in FIG. 1D, the laser locating system comprises three laser sources A. Three gauge points S may be disposed on a surface of the model body or the radiotherapy target with respect to a reference point D of the model body or the radiotherapy target. An intersection of straight lines passing through the three gauge points S is the reference point D. During positioning of the model body or the radiotherapy target, the treatment couch may be moved to ensure that three light beams emitted by the three laser sources A are respectively aligned with the three gauge points S on the surface of the model body or the body surface of the radiotherapy target. The three light beams pass through the three gauge points S respectively. At this moment, the intersection of the three light beams is the reference point D. That is, the reference point D may overlap the central point of the positioning system.

Furthermore, the radiotherapy equipment may further comprise a control system (not shown in FIG. 1B(a) or FIG. 1B(b)). The control system is a control center of the radiotherapy equipment and configured to control all other portions of the radiotherapy equipment to work together, so as to realize calibration of the radiotherapy equipment and radiotherapy of the radiotherapy target. Herein, the control system further comprises an image system configured to process an image.

After a brief introduction to the terms, the application scenarios and the implementation environments involved in the embodiments of the present disclosure, a calibration method of radiotherapy equipment provided in an embodiment of the present disclosure will be described in detail with reference to FIG. 1E.

Figure 1E:
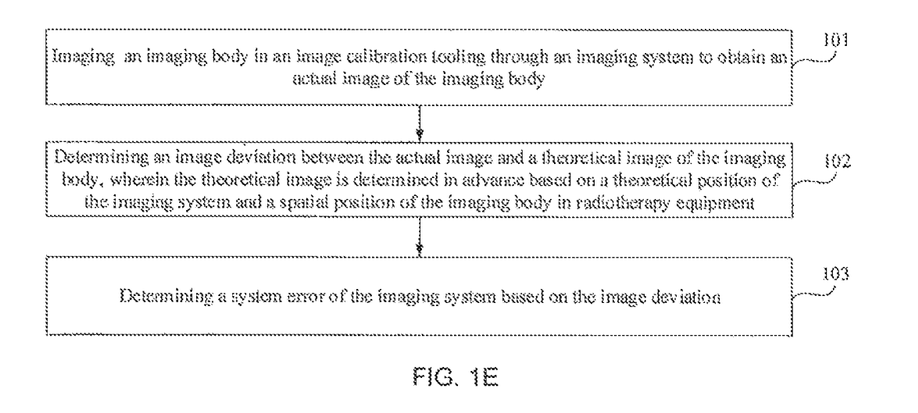
FIG. 1E is a flow chart of an error calibration method of a radiotherapy equipment provided in an embodiment of the present disclosure.

FIG. 1E is a flow chart of an error calibration method of the radiotherapy equipment, provided in an embodiment of the present disclosure. The error calibration method may calibrate the radiotherapy equipment by means of the above-mentioned image calibration tooling. As shown in FIG. 1E, the error calibration method comprises the following steps.

Step 101: an imaging body in an image calibration tooling is imaged through an imaging system to obtain an actual image of the imaging body.

Calibration of the imaging system is a basis for calibration of the radiotherapy equipment. In the embodiments of the present disclosure, the image calibration tooling as shown in FIG. 1B(a) and FIG. 1B(b) may be utilized to calibrate the imaging system. To realize calibration, the imaging body in the image calibration tooling may be imaged by means of the imaging system first.

As shown in FIG. 1B(a) and FIG. 1B(b), the imaging system 3 comprises an imaging source 31 and a flat panel detector 32 opposite to the imaging source. After the imaging system is started up, the imaging source 31 may emit x rays which irradiate the imaging body in the image calibration tooling 5 and be transmitted onto the flat panel detector 32 through the imaging body. The flat panel detector 32 may detect the x rays that penetrate the imaging body and send a detection signal to an image system of the radiotherapy equipment. The image system may generate an actual image of the imaging body according to the received detection signal.

Furthermore, during a process of calibrating the radiotherapy equipment, the imaging system may also be driven by a rack to rotate around an isocenter of the radiotherapy equipment. In this process, the imaging body may be imaged by means of the imaging system at different rotation angles to obtain actual images of the imaging body at different rotation angles. Then, image deviations between the actual images and theoretical images of the imaging body at different rotation angles are determined respectively. Based on the image deviations at the different rotation angles, system errors of the imaging system at the different rotation angles are determined respectively.

If the actual images of the imaging body at different rotation angles are deviated, it indicates that the imaging system has a relative position error in the rotation process. That is, the treatment head, the image calibration tooling or the flat panel detector has moved relative to the rack. The movement may be caused by looseness of a fixing piece of the treatment head, the image calibration tooling or the flat panel detector. Thus, the position of the treatment head, the image calibration tooling or the flat panel detector may be adjusted and the fixing piece may be fastened first according to the system errors of the imaging system at the different rotation angles to perform preliminary error correction.

It should be noted that in the embodiments of the present disclosure, one or more imaging bodies in the image calibration tooling may be imaged to complete the calibration of the imaging system. In practice, in order to improve the calibration accuracy, the plurality of imaging bodies may be imaged to obtain their actual images. Then, the subsequent operations may be performed according to the actual images of the plurality of imaging bodies. Through imaging the plurality of imaging bodies, not only a position error but also an angle error of the imaging system may be obtained. Thus, the system error of the imaging system can be calibrated more accurately.

Step 102: an image deviation between the actual image and a theoretical image of the imaging body is determined, wherein the theoretical image is determined in advance based on a theoretical position of the imaging system and a spatial position of the imaging body in radiotherapy equipment.

Before calibration, the theoretical image of the imaging body may be determined based on the theoretical position of the imaging system and the spatial position of the imaging body of the image calibration tooling in the rack. After being obtained, the actual image of the imaging body may be compared with the stored theoretical image to obtain an image deviation therebetween. The image deviation comprises an image position deviation, an image shape deviation, etc.

Specifically, the theoretical image of the imaging body may be determined based on a position relationship between the imaging body and the isocenter of the radiotherapy equipment. In this way, the locating accuracy of the imaging system may be based on the fact that the isocenter of the radiotherapy equipment is taken as the reference point. Therefore, the locating accuracy of the imaging system and the accuracy of the isocenter of the radiotherapy equipment are directly linked together. There is no need to take the treatment couch as an intermediate transfer link. Accordingly, an impact on the locating accuracy of the imaging system from the treatment couch may be removed.

In practice, the step 102 may be implemented by the image system of the control system. That is, the theoretical image of the imaging body may be generated by and stored in the image system in advance. Then, the actual image and the stored theoretical image of the imaging body are compared in the image system to obtain the image deviation.

Step 103: a system error of the imaging system is determined based on the image deviation.

In the embodiments of the present disclosure, an error calculation model may be established in advance based on a corresponding relationship between the image deviation and various system errors of the imaging system. After that, the system errors of the imaging system are determined based on the image deviation and the error calculation model.

Herein, the system errors of the imaging system may comprise a position error of the imaging source, a position error of the flat panel detector, a rotation angle error of the imaging source, an inclination angle error of the flat panel detector, etc.

Once the system error of the imaging system is determined, calibration of the imaging system is completed. Furthermore, after the system error of the imaging system is calibrated, the imaging system may be adjusted according to its system error for error collection. Alternatively, error compensation may be performed on an image in the imaging process of the imaging system. Through error correction and error compensation, the imaging accuracy of the imaging system may be improved.

In the embodiments of the present disclosure, the imaging body disposed within the preset distance range of the isocenter of the radiotherapy equipment may be adopted to perform error calibration on the radiotherapy equipment. During the calibration process, the imaging body can be directly imaged through the imaging system. Then, the system error of the imaging system may be determined based on the image deviation between the actual image and the theoretical image of the imaging body. In the present disclosure, as the imaging system is calibrated in an image-guided mode, it is no need to position the model body and move the treatment couch during the calibration process, thereby avoiding the influence of positioning system error or the treatment couch's position accuracy on the calibration accuracy of the imaging system, which improves the accuracy and efficiency of the calibration.

In another embodiment, an imaging system may be utilized to calibrate a positioning system. However, as there may be an image deviation in an imaging system which is not calibrated, the positioning may be inaccurately calibrated. Thus, in order to improve the accuracy, an image calibration tooling may be utilized firstly to calibrate the imaging system. Then, the calibrated imaging system may be utilized to calibrate the positioning system. A calibration method of the positioning system will be described in detail with reference to FIG. 2A by taking the calibrated imaging system which is utilized to calibrate the positioning system as an example.

Figure 2A:
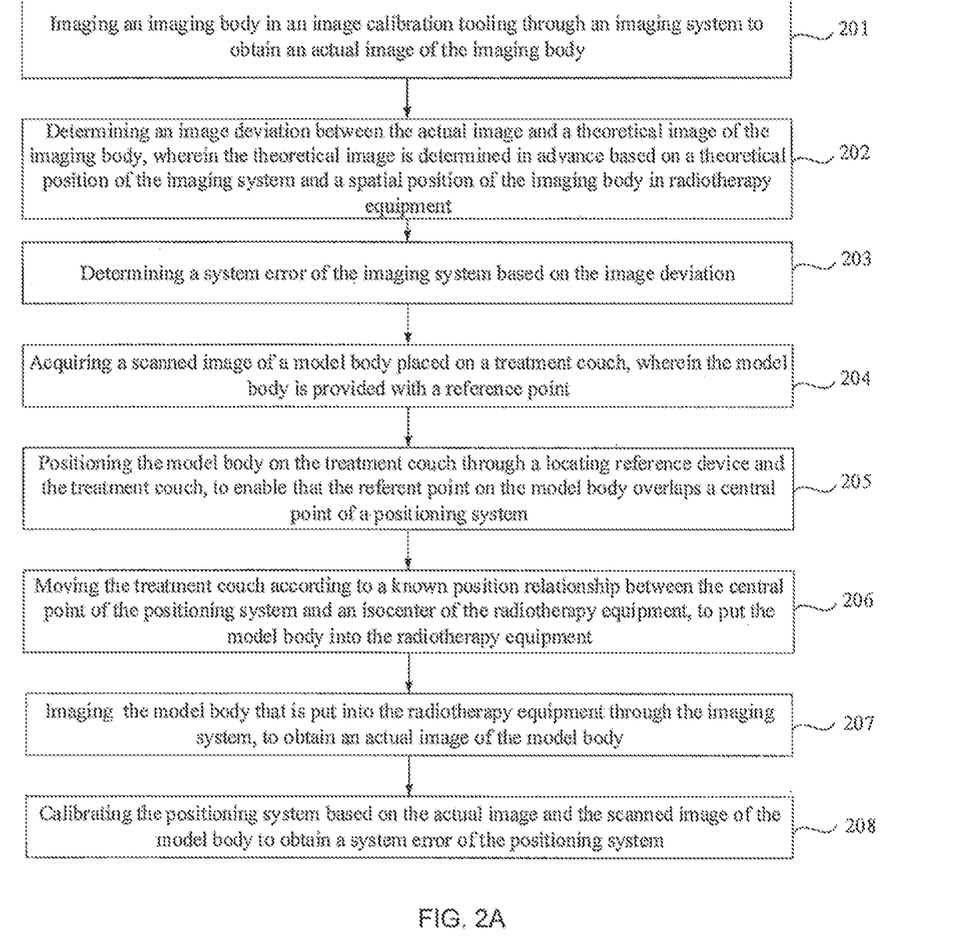
FIG. 2A is a flow chart of another error calibration method of a radiotherapy equipment, provided in an embodiment of the present disclosure.

FIG. 2A is a flow chart of another error calibration method of radiotherapy equipment, provided in an embodiment of the present disclosure. As shown in FIG. 2A, the error calibration method comprises the following steps.

Step 201: an imaging body in an image calibration tooling is imaged through an imaging system to obtain an actual image of the imaging body.

Step 202: an image deviation between the actual image and a theoretical image of the imaging body is determined, wherein the theoretical image is determined in advance based on a theoretical position of the imaging system and a spatial position of the imaging body in radiotherapy equipment.

Step 203: a system error of the imaging system is determined based on the image deviation.

Herein, the specific implementations of the steps 201 to 203 may refer to related descriptions in the above-mentioned steps 101 to 103, which are not repeated here.

Step 204: a scanned image of a model body placed on a treatment couch is acquired, wherein the model body is provided with a reference point.

In the embodiments of the present disclosure, calibration of the positioning system may be accomplished by means of the model body. Here, the reference point, which is a point required to be located by the positioning system, is disposed on the model body.

In practice, a plurality of gauge points may be disposed on the surface of the model body in advance according to the determined position of the reference point. Alternatively, a plurality of gauge points are disposed on the surface of the model body and an imaging marker such as a gold marker is placed in the model body, such that in the subsequent positioning or imaging process, the position of the reference point may be determined according to the plurality of gauge points on the surface of the model body, or the plurality of gauge points on the surface of the model body and the imaging marker in the model body.

Herein, the scanned image of the model body may be acquired from a scanning device other than the radiotherapy equipment. That is, before calibration of the positioning system, the model body placed on the treatment couch may be scanned by means of the scanning device to obtain the scanned image of the model body.

Herein, the scanning device may be a CT (Computed Tomography) scanner, an MR (Magnetic Resonance) scanner, a PET (Position Emission Tomography) scanner, an ultrasonic scanning device or the like. Correspondingly, the scanned image that is obtained may be a CT scanned image, an MR scanned image, a PET scanned image, an ultrasonic scanned image or the like. For example, the model body placed on the treatment couch may be scanned by means of the CT scanner to obtain the CT scanned image of the model body.

Taking that the plurality of gauge points are disposed on the surface of the model body as an example, after the scanned image of the model body is obtained, the scanning device may determine the reference point of the model body based on the plurality of gauge points on the surface of the model body in the scanned image by means of an image processing system or TPS (Transaction Processing Systems), and obtain coordinates of the reference point. After that, the scanning device may send the scanned image of the model body and the coordinates of the reference point to the control system of the radiotherapy equipment, such that the radiotherapy equipment may calibrate the positioning system based on the scanned image of the model body and the coordinates of the reference point.

Step 205: the model body on the treatment couch is positioned through a locating reference device and the treatment couch, to enable that the referent point on the model body overlaps a central point of a positioning system.

The locating reference device may locate the reference point of the model body according to the plurality of gauge points on the surface of the model body. The treatment couch may be moved to enable that the reference point on the model body overlaps the central point of the positioning system.

Step 206: the treatment couch is moved according to a known position relationship between the central point of the positioning system and an isocenter of the radiotherapy equipment, to put the model body into the radiotherapy equipment.

The treatment couch is moved based on the known position relationship between the central point of the positioning system and the isocenter of the radiotherapy equipment, such that the central point of the positioning system may spatially overlap the isocenter of the radiotherapy equipment. In practice, the central point of the positioning system and the isocenter of the radiotherapy equipment are usually located in a Y-axis position as shown in FIG. 1B(b) and are at a certain distance away from each other. Therefore, according to a known distance between the central point of the positioning system and the isocenter of the radiotherapy equipment, the treatment couch can be moved by the positioning system in the minus Y-axis direction for the certain distance, such that the central point of the positioning system may overlap the isocenter of the radiotherapy equipment. Furthermore, the reference point of the model body overlaps the isocenter of the radiotherapy equipment.

Step 207: the model body that is put into the radiotherapy equipment is imaged through the imaging system, to obtain an actual image of the model body.

Herein, the actual image of the model body comprises a position of the reference point. The model body that is put into the radiotherapy equipment is imaged through the imaging system to obtain the actual image of the model body comprises the following two implementations.

A first implementation: the imaging system is adjusted based on the system error of the imaging system for error correction; and the model body that is put into the radiotherapy equipment may be imaged by means of the imaging system subjected to error correction to obtain the actual image of the model body.

Herein, adjusting the imaging system comprises: adjusting, according to the system error of the imaging system, the position of the imaging source, the position of the flat panel detector, the rotation angle of the imaging source, the inclination angle of the flat panel detector, etc.

That is, in the first implementation, after the system error of the imaging system is calibrated, the position and/or the angle of the imaging source and/or the flat panel detector in the imaging system may be directly adjusted according to the system error. Error correction may be performed on a hardware system of the imaging system, so as to reduce or eliminate the system error of the imaging system in hardware as much as possible, and ensure the imaging accuracy of the imaging system.

A second implementation: the model body in the radiotherapy equipment is imaged by means of the imaging system to obtain an initial image of the model body; error compensation is performed on the initial image of the model body based on the system error of the imaging system; and the initial image of which error compensation is accomplished is determined as the actual image of the model body.

Since the imaging system of which the hardware system is not subjected to error correction may have the system error, the initial image obtained by means of the imaging system may have a deviation. To eliminate this deviation, error compensation may be performed on the initial image of the model body based on the system error, calibrated in the above step 203, of the imaging system. That is, the initial image of the model body may be adjusted according to the system error of the imaging system, such that the deviation may be eliminated through image processing.

That is, in the second implementation, after the system error of the imaging system is calibrated, error compensation may be performed on the initial image of the model body according to the calibrated system error in the imaging process of the imaging system, instead of being performed on the hardware system of the imaging system. Thus, an image error may be eliminated through image processing.

Step 208: the positioning system is calibrated based on the actual image and the scanned image of the model body to obtain a system error of the positioning system.

Herein, the positioning system is calibrated based on the actual image and the scanned image of the model body may comprise the following steps (1) to (4).

(1) The actual image or the scanned image of the model body is moved until a first area in the actual image a second area in the scanned image of the model body overlap.

Herein, the first area and the second area are areas with the same content, that is, areas with the same image features. And the first area and the second area may be the whole or part of the model body, which are not limited in the embodiments of the present disclosure.

In the embodiments of the present disclosure, the actual image or the scanned image of the model body may be moved to perform image registration based on the image features, so as to ensure that the areas with the same image features in the two images overlap each other.

Figure 2B:
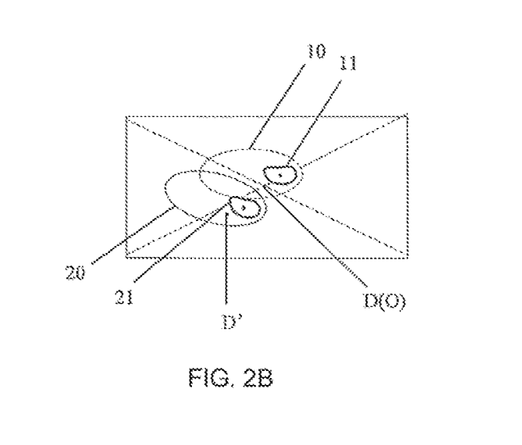
FIG. 2B is a schematic view of an actual image and a scanned image of a model body provided in an embodiment of the present disclosure.

As shown in FIG. 2B, it comprises a scanned image 10 of a model body and an actual image 20 of a model body. Herein, the scanned image 10 of the model body comprises a reference point D and a first area 11 of the model body. The actual image 20 of the model body comprises a reference point D' and a second area 21 of the model body. As the scanned image 10 and the actual image 20 of the model body have a position deviation, either the scanned image 10 or the actual image 20 of the model body may be moved to enable the first area 11 and the second area 21 to overlap each other.

(2) A first movement displacement and a first rotation angle are determined, wherein the first movement displacement and the first rotation angle respectively refer to a moved displacement and a rotated angle of the actual image or the scanned image of the model body when the first area and the second area overlap each other.

When the first area and the second area overlap, the moved displacement and the rotated angle of the actual image or the scanned image of the model body may be determined respectively. The moved displacement may be determined as the first movement displacement. The rotated angle may be determined as the first rotation angle.

Herein, the first movement displacement may comprise movement displacements in three directions, that is, movement displacements on the three coordinate axes of a three-dimensional coordinate system. The first rotation angle may comprise rotation angles in three directions, that is, angles of rotation around the above-mentioned three coordinate axes.

(3) The system error of the positioning system is determined based on the first movement displacement and the first rotation angle.

Since the first movement displacement and the first rotation angle are caused by the system error of the positioning system, the first movement displacement and the first rotation angle may be determined as the system error of the positioning system. After the system error of the positioning system is calibrated, error correction may be performed on hardware of the positioning system according to the system error. Alternatively, error compensation may be performed in the positioning process.

In the related art, calibration of a positioning system may be realized through imaging an isocenter by means of a model body loaded with a film. This method wastes time and energy and is low in calibration accuracy. In the embodiments of the present disclosure, a image-guided manner may be adopted, the positioning system may be calibrated by means of the calibrated imaging system. Error calibration may be performed by means of an image method, and therefore is convenient and quick, and high in accuracy.

Figure 3:
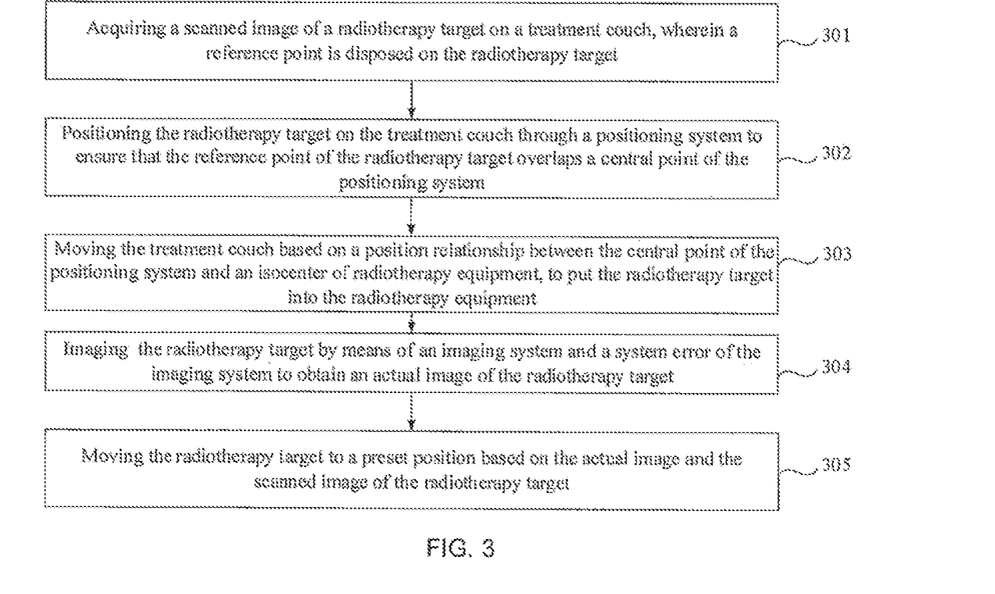
FIG. 3 is a flow chart of a positioning method of a radiotherapy target provided in an embodiment of the present disclosure.

After completion of calibration of the radiotherapy equipment, a radiotherapy target may be located by means of the calibrated imaging system and/or the calibrated positioning system. The followings will describe a location method of the radiotherapy target in detail with reference to the FIG. 3 by taking the fact that the radiotherapy target is located by means of the calibrated imaging system and the calibrated positioning system as an example FIG. 3 is a flow art of a location method of a radiotherapy target, provided in an embodiment of the present disclosure. As shown in FIG. 3, the location method comprises the following steps.

Step 301: a scanned image of a radiotherapy target on a treatment couch is acquired, wherein a reference point is disposed on the radiotherapy target.

Herein, the reference point of the radiotherapy target is a locating point which is determined in advance. In practice, a plurality of gauge points may be disposed on the body surface of the radiotherapy target according to the position of the reference point, which is determined in advance. Alternatively, a plurality of gauge points are disposed on the body surface of the radiotherapy target and an imaging marker is placed in the radiotherapy target, such that the position of the reference point of the radiotherapy target may be conveniently determined in the follow-up positioning or imaging process, according to the plurality of the gauge points on the body surface of the radiotherapy target, or the plurality of gauge points on the surface of the radiotherapy target and the imaging marker in the radiotherapy target.

A scanned image of the radiotherapy target may be acquired from a scanning device other than the radiotherapy equipment. That is, before treatment of the radiotherapy target, the scanning device may be utilized first to scan the radiotherapy target placed on the treatment couch to obtain the scanned image of the radiotherapy target.

After the scanned image of the radiotherapy target is obtained by taking the fact that the plurality of gauge points are disposed on the body surface of the radiotherapy target as an example, the scanning device may also determine the reference point of the radiotherapy target and obtain coordinates of the reference point based on the plurality of gauge points, on the surface of the radiotherapy target, in the scanned image. After that, the scanned image of the radiotherapy target and the coordinates of the reference point may be transmitted to a control system of the radiotherapy equipment.

Step 302: the radiotherapy target on the treatment couch is positioned through a positioning system to ensure that the reference point of the radiotherapy target overlaps a central point of the positioning system.

Herein, the radiotherapy target on the treatment couch is positioned through the positioning system and the system error thereof comprises the following two implementations.

A first implementation: the positioning system is adjusted by means of the system error of the positioning system for error correction; and the radiotherapy target on the treatment couch is positioned by means of the positioning system subjected to error correction to ensure that the reference point of the radiotherapy target overlaps the central point of the positioning system.

Herein, the system error of the positioning system comprises a position error and an angle error. Factors that cause the system error of the positioning system comprise a position error and an angle error of a locating reference device and a displacement deviation of the treatment couch. Therefore, when the positioning system is adjusted, the position and the angle of the locating reference device of the positioning system may be adjusted according to the system error of the positioning system, or the position of the treatment couch may be adjusted, so as to eliminate an error of the positioning system in terms of hardware. For example, a position and an angle of a laser lamp may be adjusted according to the system error of the positioning system when the locating reference device is a laser locating system.

When the body position of the radiotherapy target on the treatment couch is positioned by means of the positioning system subjected to error correction, accurate positioning may be realized. Thus, the reference point of the radiotherapy target accurately overlaps the central point of the positioning system.

A second implementation: the body position of the radiotherapy target on the treatment couch is positioned by means of the positioning system. In the positioning process, error compensation may be performed on the positioning process based on the system error of the positioning system.

That is, in the second implementation, after the system error of the positioning system is obtained, error compensation can be performed in software, instead of being performed on the hardware system of the positioning system. In practice, coordinates of the treatment couch or a position parameter of the body surface imaging system are corrected according to the system error of the positioning system so as to perform error compensation on the positioning process of the positioning system.

Herein, the system error of the positioning system is obtained through calibrating the positioning system by means of the calibration method provided in the embodiment illustrated by FIG. 2A.

Step 303: the treatment couch is moved based on a position relationship between the central point of the positioning system and an isocenter of radiotherapy equipment, to put the radiotherapy target into the radiotherapy equipment.

Moving the treatment couch based on the position relationship between the central point of the positioning system and the isocenter of the radiotherapy equipment is to ensure that the central point of the positioning system overlaps the isocenter of the radiotherapy equipment. Furthermore, the reference point of the radiotherapy target overlaps the isocenter of the radiotherapy equipment, such that radiotherapy treatment may be performed on the reference point through the radiotherapy equipment.

It should be noted that the embodiments of the present disclosure only take the fact that the reference point and a therapeutic target of the radiotherapy target are in the same position as an example. In practice, the reference point and the therapeutic target of the radiotherapy target may be in different positions. When they are in different positions, after the reference point of the radiotherapy target overlaps the isocenter of the radiotherapy equipment in step 303, the treatment couch may be continually moved based on the position relationship between the reference point and the therapeutic target of the radiotherapy target to ensure that the therapeutic target overlaps the isocenter of the radiotherapy equipment.

In view of changes of the positioning accuracy or movement and deformation of human internal organs during the use process of the positioning system, for example, since the treatment couch may have a movement error, in the process that the reference point or the therapeutic target of the radiotherapy target is moved to the isocenter of the radiotherapy equipment by moving the treatment couch, the radiotherapy target may not be accurately moved to the preset position. That is, the radiotherapy target may not be accurately located. In the embodiments of the present disclosure, in order to ensure the locating accuracy of the radiotherapy target, image-guided positioning may be performed on the radiotherapy target at a time. That is, the following step is added on the basis of steps 301 to 303.

Step 304: the radiotherapy target is imaged by means of an imaging system and a system error of the imaging system to obtain an actual image of the radiotherapy target.

The radiotherapy target is imaged by means of the imaging system and the system error of the imaging system has the same principle as that in step 207, and may also comprise the following two implementations.

A first implementation: the imaging system is adjusted based on the system error of the imaging system for error correction; and the radiotherapy target is imaged by means of the imaging system subjected to error correction to obtain the actual image of the radiotherapy target.

A second implementation: the radiotherapy target is imaged by means of the imaging system to obtain the initial image of the radiotherapy target; error compensation is performed on the initial image of the radiotherapy target based on the system error of the imaging system; and the initial image of which error compensation is accomplished is determined as the actual image of the radiotherapy target.

The system error of the imaging system is obtained by calibrating the imaging system by means of the calibration method of the embodiment illustrated by FIG. 1E.

Step 305: the radiotherapy target is moved to a preset position based on the actual image and the scanned image of the radiotherapy target.

The preset position is a position where the radiotherapy target is located when the reference point or the therapeutic target of the radiotherapy target overlaps the isocenter of the radiotherapy equipment.

The radiotherapy target is moved to the preset position based on the actual image and the scanned image of the radiotherapy target may comprise the following steps (1) to (3).

(1) The actual image or the scanned image of the radiotherapy target is moved until a third area in the actual image of the radiotherapy target overlaps a fourth area in the scanned image of the radiotherapy target. The third area and the fourth area are areas with the same content.

The third area and the fourth area are areas with the same content, that is, areas with the same image features, and may be the whole or part of the radiotherapy target, which are not limited in the embodiments of the present disclosure. In practice, the third area, as well as the fourth area, may be an area including a therapeutic target.

In the embodiments of the present disclosure, the actual image or the scanned image of the radiotherapy target may be moved for image registration based on the image features to ensure that the areas with the same image features in the two images overlap each other (2) A second movement displacement and a second rotation angle are determined and respectively mean a moved displacement and a rotated angle of the actual image or the scanned image of the radiotherapy target when the third area and the fourth area overlap each other.

When the third area and the fourth area overlap each other, the moved displacement and the rotated angle of the actual image or the scanned image of the radiotherapy target may be determined respectively. The moved displacement is determined as the second movement displacement. The rotated angle is determined as the second rotation angle The second movement displacement may comprise movement displacements in three directions, that is, movement displacements on the three coordinate axes of a three-dimensional coordinate system. The second rotation angle may comprise rotation angles in three directions, that is, angles of rotation around the above-mentioned three coordinate axes.

(3) The treatment couch is moved based on the second movement displacement and rotated based on the second rotation angle to move the radiotherapy target to the preset position.

Specifically, if the actual image of the radiotherapy target is moved in step (1), the treatment couch may be moved in a positive direction according to the second movement displacement in step (3) and rotated in a positive direction according to the second rotation angle; and if the scanned image of the radiotherapy target is moved in step (1), the treatment couch may be moved in a negative direction according to the second movement displacement and rotated in a negative direction according to the second rotation angle.

After the treatment couch is moved based on the second movement displacement and rotated based on the second rotation angle, the radiotherapy target may be accurately located. That is, the reference point or the therapeutic target of the radiotherapy target may be located at the isocenter of the radiotherapy equipment.

In the embodiments of the present disclosure, as the radiotherapy target is located by means of the calibrated imaging system and the calibrated positioning system, a movement error of the treatment couch in the locating process is eliminated. The locating accuracy is improved. A demand on the movement accuracy of the treatment couch is lowered. Accordingly, a manufacturing cost of the treatment couch is reduced.

It should be noted that the embodiments of the present disclosure only take the fact that the radiotherapy target is located by means of the imaging system calibrated by the method illustrated by FIG. 1E and the positioning system calibrated by the method illustrated by FIG. 2A as an example for explanation. In practice, the radiotherapy target may be located by means of the imaging system calibrated by the method illustrated by FIG. 1E and the uncalibrated positioning system, or by means of the imaging system calibrated by the method illustrated by FIG. 1E and the positioning system calibrated by other methods, which are not limited in the embodiments of the present disclosure.

After the detailed descriptions of the calibration method of the imaging system, the calibration method of the positioning system and the positioning method of the radiotherapy target, a calibration device of radiotherapy equipment and a positioning device of a radiotherapy target, provided by the embodiments of the present disclosure are introduced in detail with reference to the drawings.

Figure 4:
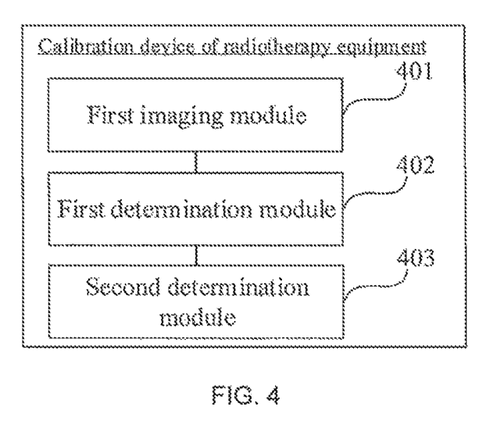
FIG. 4 is a schematic view of a structure of an error calibration device of a radiotherapy equipment provided in an embodiment of the present disclosure.
Figure 5:
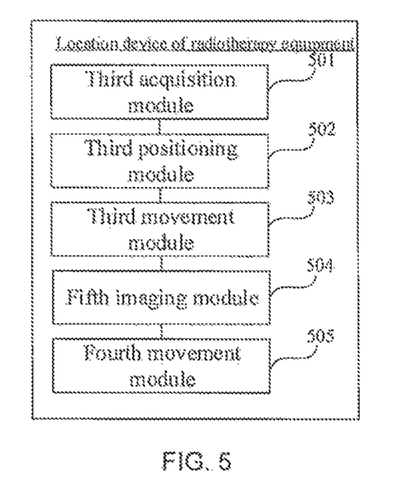
FIG. 5 is a schematic view of a structure of an error location device of a radiotherapy equipment provided in an embodiment of the present disclosure.

FIG. 4 is a schematic view of a structure of an error calibration device of a radiotherapy equipment provided by an embodiment of the present disclosure. The error calibration device may be realized through software, hardware or a combination thereof. Referring to FIG. 4, the error calibration device may include:

A first imaging module 401 configured to execute an operation executed by step 101 in the embodiment illustrated by FIG. 1E and an operation executed by step 201 in the embodiment illustrated in FIG. 2A;

A first determination module 402 configured to execute an operation executed by step 102 in the embodiment illustrated by FIG. 1E and an operation executed by step 202 in the embodiment illustrated in FIG. 2A;

A second determination module 403 configured to execute an operation executed by step 103 in the embodiment illustrated by FIG. 1E and an operation executed by step 203 in the embodiment illustrated in FIG. 2A;

FIG. 5 is a schematic view of a structure of an error calibration device of a radiotherapy target provided in an embodiment of the present disclosure. The calibration device illustrated by FIG. 4 is adopted in the error calibration device, so as to accomplish the positioning of the radiotherapy target of the radiotherapy equipment. The error calibration device may be realized through software, hardware or a combination thereof. Referring to FIG. 5, the error calibration device may comprise:

a third acquisition module 501 configured to execute an operation executed by the step 301 in the embodiment illustrated by FIG. 3;

a third positioning module 502 configured to execute an operation executed by the step 302 in the embodiment illustrated by FIG. 3;

a third movement module 503 configured to execute an operation executed by the step 303 in the embodiment illustrated by FIG. 3;

a fifth imaging module 504 configured to execute an operation executed by the step 304 in the embodiment illustrated by FIG. 3; and a fourth movement module configured to execute an operation executed by the step 305 in the embodiment illustrated by FIG. 3.

It should be noted that when the calibration device of the radiotherapy equipment and the locating device of the radiotherapy target, provided in the embodiments of the present disclosure, realize calibration of the radiotherapy equipment and location of the radiotherapy target, only division of the above-mentioned function modules is illustrated. In practice, functions may be allocated to be accomplished by the different function modules as required. That is, the internal structures of the devices are divided into the different function modules to accomplish all or part of the above-described functions. In addition, the calibration device and the calibration method of the radiotherapy equipment, as well as the locating device and the location method of the radiotherapy target, provided by the embodiments of the present disclosure, belong to the same conception. Their specific implementation processes are described in method embodiments and will not be repeated herein.

All or part of the above embodiments may be realized through software, hardware, firmware or any combinations thereof. When realized through software, all or part of the embodiments may be realized in the format of a computer program product which comprises one or more computer instructions. All or part of the computer instructions are loaded and executed on a computer according to the flow or functions of the embodiments of the present disclosure. The computer may be a universal computer, a dedicated computer, a computer network or other programmable devices. The computer instructions may be stored in the computer readable storage medium or transmitted from one computer readable storage medium to another. For example, the computer instructions may be transmitted from a website, a computer, a server or a data center to another website, computer, server or data center in a wired (such as a coaxial cable, an optical fiber and a digital subscriber line (DSL)) or wireless (such as infrared, wireless and microwaves) manner. The computer readable storage medium may be any available medium that may be accessed by the computer. Or, the computer readable storage medium may be data storage equipment such as a server and a data center integrated with one or more available media. The available medium may be a magnetic medium (such as a floppy disk, a hard disk or a magnetic tape), an optical medium (for example, a digital versatile disc (DVD)), a semiconductor medium (for example, a solid state hard disk (SSD)), or the like That is, the embodiment of the present disclosure provides a computer readable storage medium and a computer program product containing an instruction.

The instruction is stored in the computer readable storage medium. When the instruction runs on a computer, the computer executes the method of any of the embodiments in FIG. 1E, FIG. 2A and FIG. 3.

When the computer program product including the instruction runs on a computer, the computer executes the method of any of the embodiments in FIG. 1E, FIG. 2A and FIG. 3.

It should be understood by those skilled in the art that, all or part of the steps for implementing the above embodiments may be accomplished through hardware, or through programs that instruct related hardware. The programs may be stored in a computer-readable storage medium. The above-mentioned storage medium may be a ready-only memory, a magnetic disk, a light disk, or the like.

The foregoing descriptions are only embodiments provided by the present disclosure, and do not intend to limit the present disclosure. Any variation, equivalent substitution and modification that fall within the spirit and principle of the present disclosure shall be embraced by the protection scope of the present disclosure.

What is claimed is:

1. An error calibration method of radiotherapy equipment comprising an imaging system, wherein an imaging body disposed within a preset distance range of an isocenter of the radiotherapy equipment is adopted for error calibration of the radiotherapy equipment, and the error calibration method comprises:
   imaging the imaging body through the imaging system to obtain an actual image of the imaging body;
   determining an image deviation between the actual image and a theoretical image of the imaging body, the theoretical image being obtained in advance based on a theoretical position of the imaging system and a spatial position of the imaging body in the radiotherapy equipment; and
   determining a system error of the imaging system based on the image deviation,
   wherein the radiotherapy equipment further comprises a positioning system, and the positioning system comprises a locating reference device and a treatment couch; and
   after determining the system error of the imaging system based on the image deviation, the error calibration method further comprises:
   adjusting the imaging system based on the system error of the imaging system for error correction;
   acquiring a scanned image of a model body placed on the treatment couch, the model body being provided with a reference point thereon;
   positioning the model body on the treatment couch through the locating reference device and the treatment couch, to enable that the reference point on the model body overlaps a central point of the positioning system;
   moving the treatment couch based on a position relationship between the central point of the positioning system and the isocenter of the radiotherapy equipment, to put the model body into the radiotherapy equipment;
   imaging the model body that is put into the radiotherapy equipment through the imaging system subjected to the error correction to obtain an actual image of the model body; and
   calibrating the positioning system based on the actual image and the scanned image of the model body to obtain a system error of the positioning system.

2. The error calibration method according to claim 1, wherein calibrating the positioning system based on the actual image and the scanned image of the model body comprises:
   moving one of the actual image and the scanned image of the model body until a first area in the actual image of the model body overlaps a second area in the scanned image of the model body, wherein the first area and the second area are areas with the same content;
   determining a first movement displacement and a first rotation angle, wherein the first movement displacement and the first rotation angle respectively refer to a moved displacement and a rotated angle of one of the actual image and the scanned image of the model body when the first area and the second area overlap with each other; and
   determining the system error of the positioning system based on the first movement displacement and the first rotation angle.

3. The error calibration method according to claim 1, wherein the radiotherapy equipment further comprises a rack on which the imaging system is disposed; the rack drives the imaging system to rotate around the isocenter of the radiotherapy equipment; and the error calibration method further comprises:
   driving the imaging system to rotate around the isocenter of the radiotherapy equipment through the rack;
   imaging the imaging body at different rotation angles through the imaging system, when the rack drives the imaging system to rotate around the isocenter of the radiotherapy equipment, to obtain actual images of the imaging body at different rotation angles;
   determining image deviations between the actual images and theoretical images of the imaging body at different rotation angles respectively; and
   determining system errors of the imaging system at different rotation angles based on the image deviations at different rotation angles respectively.

4. A location method of a radiotherapy target, wherein radiotherapy equipment of which calibration is accomplished by the error calibration method according to claim 1 is adopted to locate the radiotherapy target; and the location method comprises:
   acquiring a scanned image of the radiotherapy target placed on the treatment couch, the radiotherapy target being provided with a reference point thereon;
   positioning the radiotherapy target on the treatment couch through the positioning system to enable that the reference point on the radiotherapy target overlaps a central point of the positioning system;
   moving the treatment couch based on the position relationship between the central point of the positioning system and the isocenter of the radiotherapy equipment, to put the radiotherapy target into the radiotherapy equipment;
   imaging the radiotherapy target through the imaging system to obtain an actual image of the radiotherapy target; and moving the radiotherapy target to a preset position based on the actual image and the scanned image of the radiotherapy target.

5. The location method according to claim 4, wherein positioning the radiotherapy target on the treatment couch through the positioning system comprises one of the following steps:
adjusting the positioning system based on the system error of the positioning system for error correction; and positioning the radiotherapy target on the treatment couch through the positioning system subjected to error correction; and
positioning the radiotherapy target on the treatment couch through the positioning system, and performing error compensation based on the system error of the positioning system in the positioning process.

6. The location method according to claim 4, wherein imaging the radiotherapy target through the imaging system to obtain an actual image of the radiotherapy target comprises one of the following steps:
adjusting the imaging system based on the system error of the imaging system for error correction; and imaging the radiotherapy target through the imaging system subjected to error correction to obtain the actual image of the radiotherapy target; and
imaging the radiotherapy target through the imaging system to obtain an initial image of the radiotherapy target; performing error compensation on the initial image of the radiotherapy target based on the system error of the imaging system; and determining the initial image of which the error compensation is accomplished as the actual image of the radiotherapy target.

7. An error calibration method of radiotherapy equipment comprising an imaging system, wherein an imaging body disposed within a preset distance range of an isocenter of the radiotherapy equipment is adopted for error calibration of the radiotherapy equipment, and the error calibration method comprises:
imaging the imaging body through the imaging system to obtain an actual image of the imaging body;
determining an image deviation between the actual image and a theoretical image of the imaging body, the theoretical image being obtained in advance based on a theoretical position of the imaging system and a spatial position of the imaging body in the radiotherapy equipment; and
determining a system error of the imaging system based on the image deviation,
wherein the radiotherapy equipment further comprises a positioning system, and the positioning system comprises a locating reference device and a treatment couch; and
after determining the system error of the imaging system based on the image deviation, the error calibration method further comprises:
acquiring a scanned image of a model body placed on the treatment couch, the model body being provided with a reference point thereon;
positioning the model body on the treatment couch through the locating reference device and the treatment couch to enable that the reference point on the model body overlaps a central point of the positioning system;
moving the treatment couch based on a position relationship between the central point of the positioning system and the isocenter of the radiotherapy equipment, to put the model body into the radiotherapy equipment;
imaging the model body that is put into the radiotherapy equipment through the imaging system to obtain an initial image of the model body;
performing error compensation on the initial image of the model body based on the system error of the imaging system;
determining the initial image of which the error compensation is accomplished as an actual image of the model body; and
calibrating the positioning system based on the actual image and the scanned image of the model body to obtain a system error of the positioning system.

8. The error calibration method according to claim 7, wherein calibrating the positioning system based on the actual image and the scanned image of the model body comprises:
moving one of the actual image and the scanned image of the model body until a first area in the actual image of the model body overlaps a second area in the scanned image of the model body, wherein the first area and the second area are areas with the same content;
determining a first movement displacement and a first rotation angle, wherein the first movement displacement and the first rotation angle respectively refer to a moved displacement and a rotated angle of one of the actual image and the scanned image of the model body when the first area and the second area overlap with each other; and
determining the system error of the positioning system based on the first movement displacement and the first rotation angle.

9. A location method of a radiotherapy target, wherein radiotherapy equipment of which calibration is accomplished by the error calibration method according to claim 7 is adopted to locate the radiotherapy target; and the location method comprises:
acquiring a scanned image of the radiotherapy target placed on the treatment couch, the radiotherapy target being provided with a reference point thereon;
positioning the radiotherapy target on the treatment couch through the positioning system to enable that the reference point on the radiotherapy target overlaps a central point of the positioning system;
moving the treatment couch based on a position relationship between the central point of the positioning system and the isocenter of the radiotherapy equipment, to put the radiotherapy target into the radiotherapy equipment;
imaging the radiotherapy target through the imaging system to obtain an actual image of the radiotherapy target; and
moving the radiotherapy target to a preset position based on the actual image and the scanned image of the radiotherapy target.

10. The location method according to claim 9, wherein positioning the radiotherapy target on the treatment couch through the positioning system comprises one of the following steps:
adjusting the positioning system based on the system error of the positioning system for error correction; and positioning the radiotherapy target on the treatment couch through the positioning system subjected to error correction; and
positioning the radiotherapy target on the treatment couch through the positioning system, and performing error compensation based on the system error of the positioning system in the positioning process.

11. A non-transitory computer readable storage medium, wherein an instruction is stored in the computer readable storage medium; and when the computer readable storage medium runs on a computer, the computer executes an error calibration method of radiotherapy equipment comprising an imaging system, wherein an imaging body disposed within a preset distance range of an isocenter of the radiotherapy equipment is adopted for error calibration of the radiotherapy equipment, and the error calibration method comprises:

imaging the imaging body through the imaging system to obtain an actual image of the imaging body;

determining an image deviation between the actual image and a theoretical image of the imaging body, the theoretical image being obtained in advance based on a theoretical position of the imaging system and a spatial position of the imaging body in the radiotherapy equipment; and     determining a system error of the imaging system based on the image deviation, wherein the radiotherapy equipment further comprises a positioning system, and the positioning system comprises a locating reference device and a treatment couch; and     after determining the system error of the imaging system based on the image deviation, the error calibration method further comprises:

adjusting the imaging system based on the system error of the imaging system for error correction;

acquiring a scanned image of a model body placed on the treatment couch, the model body being provided with a reference point thereon;

positioning the model body on the treatment couch through the locating reference device and the treatment couch, to enable that the reference point on the model body overlaps a central point of the positioning system;

moving the treatment couch based on a position relationship between the central point of the positioning system and the isocenter of the radiotherapy equipment, to put the model body into the radiotherapy equipment;

imaging the model body that is put into the radiotherapy equipment through the imaging system subjected to the error correction to obtain an actual image of the model body; and     calibrating the positioning system based on the actual image and the scanned image of the model body to obtain a system error of the positioning system.

* * * * *